(12) United States Patent
Derr

(10) Patent No.: US 7,604,723 B2
(45) Date of Patent: Oct. 20, 2009

(54) MEASURING DEVICE WITH PENETRATING ELECTRODE

(75) Inventor: Andreas Derr, Wutöschingen (DE)

(73) Assignee: Testo AG (DE)

( * ) Notice: Subject to any disclaimer, the term of this patent is extended or adjusted under 35 U.S.C. 154(b) by 791 days.

(21) Appl. No.: 10/511,418

(22) PCT Filed: Jun. 25, 2003

(86) PCT No.: PCT/EP03/06714

§ 371 (c)(1),
(2), (4) Date: Oct. 14, 2004

(87) PCT Pub. No.: WO2004/015407

PCT Pub. Date: Feb. 19, 2004

(65) Prior Publication Data

US 2006/0108223 A1    May 25, 2006

(30) Foreign Application Priority Data

Jul. 5, 2002    (DE) ................. 102 33 901

(51) Int. Cl.
*G01N 27/36*    (2006.01)
(52) U.S. Cl. .............. 204/433; 204/406; 204/407; 204/414; 205/787.5
(58) Field of Classification Search ......... 204/416–420, 204/433; 324/446–449, 438; 205/787.5; 73/1.03; 422/82.01–82.03
See application file for complete search history.

(56) References Cited

U.S. PATENT DOCUMENTS

| | | | |
|---|---|---|---|
| 4,218,299 A | 8/1980 | Lindell et al. | |
| 4,252,124 A | 2/1981 | Maurer et al. | |
| 4,264,424 A * | 4/1981 | Niedrach | .................... 204/421 |
| 4,328,912 A * | 5/1982 | Haggar et al. | ................ 222/212 |
| 4,404,964 A * | 9/1983 | Kambara | ..................... 600/163 |
| 4,447,309 A * | 5/1984 | Morioka et al. | ............. 204/402 |
| 4,473,458 A * | 9/1984 | Schwartz et al. | ............. 204/433 |
| 4,608,148 A * | 8/1986 | Frollini et al. | .............. 204/408 |
| 4,686,011 A * | 8/1987 | Jackle | ...................... 205/787.5 |
| 5,139,641 A * | 8/1992 | Neukum | ................... 205/787.5 |
| 5,425,715 A * | 6/1995 | Dalling et al. | .............. 604/136 |
| 5,939,610 A | 8/1999 | Iwamoto et al. | |
| 6,051,392 A | 4/2000 | Ikeda et al. | |
| 2003/0057952 A1 | 3/2003 | Derr | |

FOREIGN PATENT DOCUMENTS

| | | |
|---|---|---|
| DE | 83 33 874 U1 | 4/1984 |
| DE | 38 14 634 A1 | 11/1989 |
| DE | 89 12 731 U1 | 2/1990 |

(Continued)

*Primary Examiner*—Nam X Nguyen
*Assistant Examiner*—Bach T Dinh
(74) *Attorney, Agent, or Firm*—Muirhead and Saturnelli, LLC

(57) ABSTRACT

The invention relates to a measuring device having a penetrating electrode. Said elongated electrode of the measuring device is movably mounted in axial direction thereof. In case of a load or a shock, it can absorb said load to a given degree in the housing of said measuring device. Said shock-absorbing characteristic makes it possible to largely prevent breaking of the first electrode that is preferably configured in the form of a glass electrode. The invention also relates to a measuring device, to a method for the production and the application of said measuring device.

29 Claims, 7 Drawing Sheets

FOREIGN PATENT DOCUMENTS

| | | |
|---|---|---|
| DE | 42 31 677 C2 | 1/1993 |
| DE | 199 61 210 A1 | 6/2001 |
| DE | 100 04 583 A1 | 8/2001 |
| DE | 100 34 520 A1 | 1/2002 |
| EP | 0 399 101 A1 | 11/1990 |
| EP | 0 753 737 A2 | 1/1997 |
| EP | 0 964 060 A2 | 12/1999 |
| FR | 2 618 902 A1 | 2/1989 |
| WO | WO01/57507 * | 8/2001 |

* cited by examiner

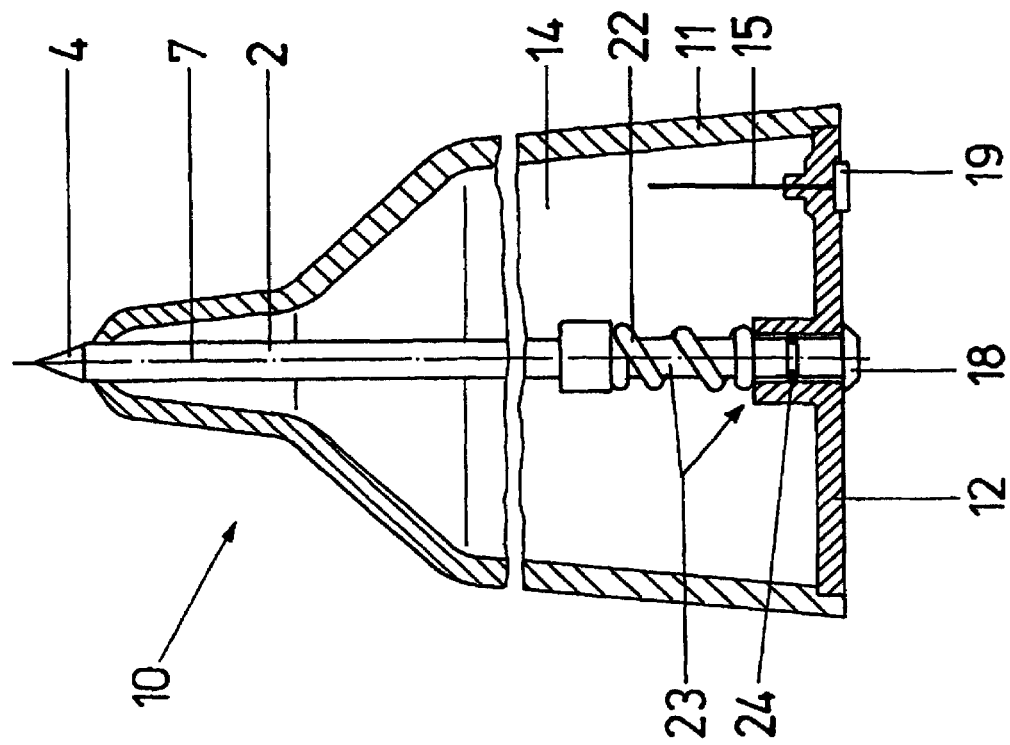
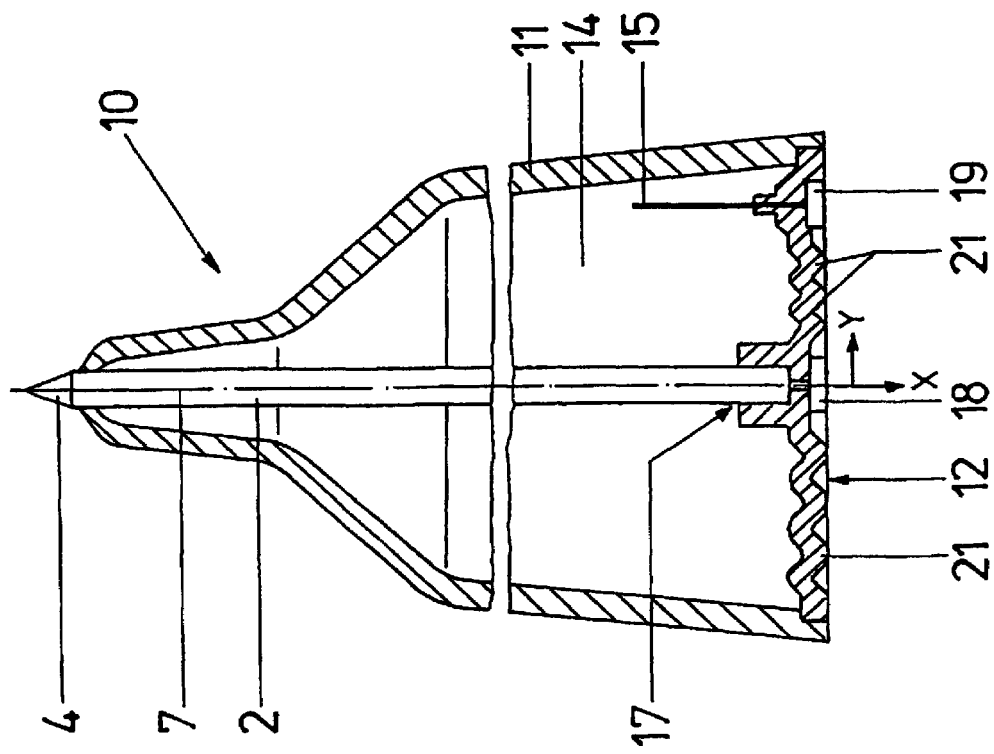

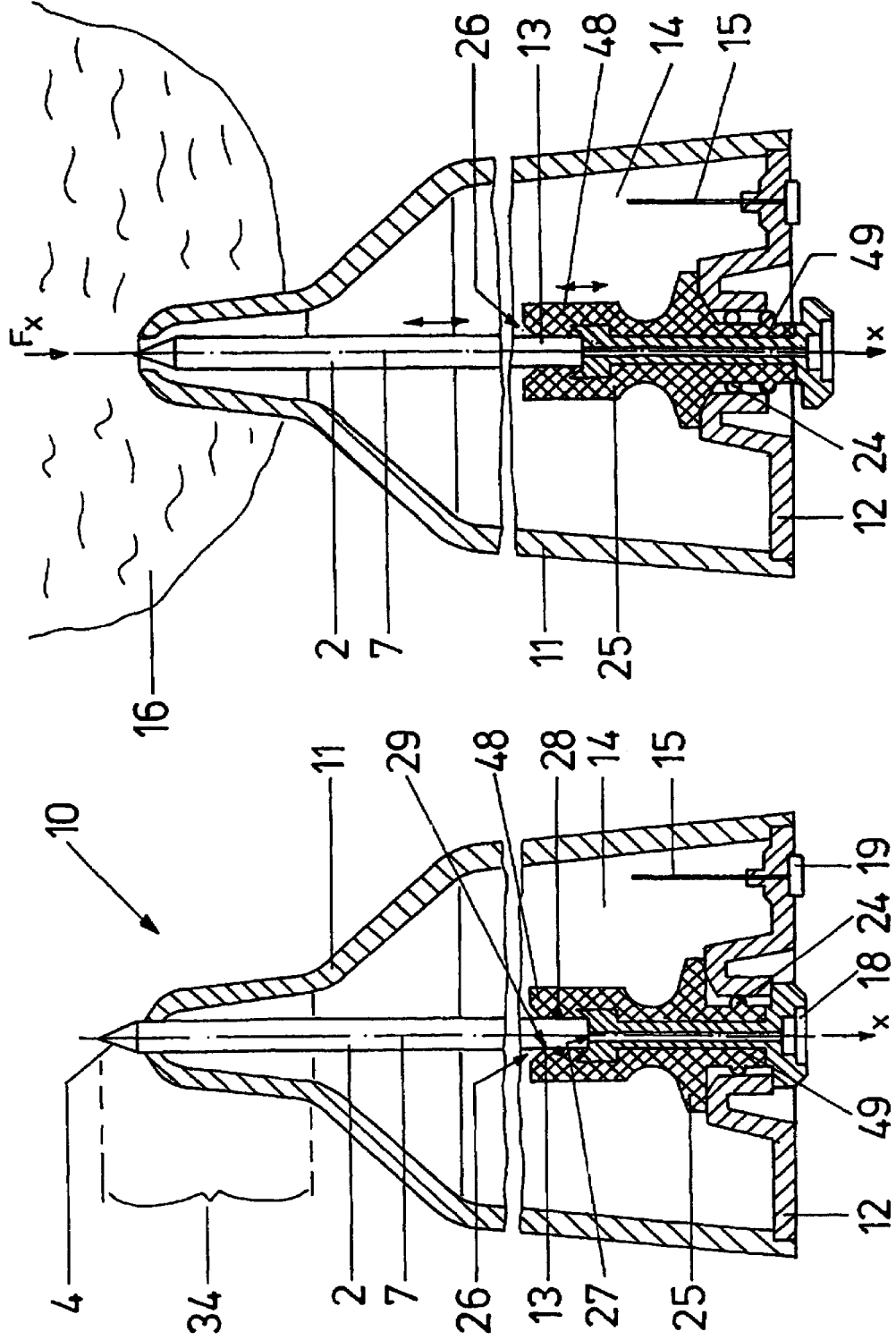

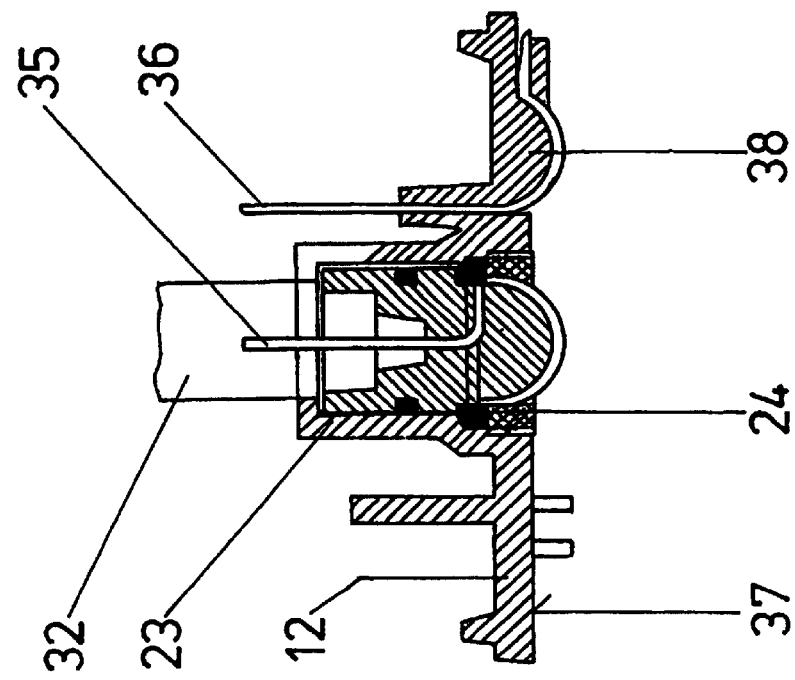
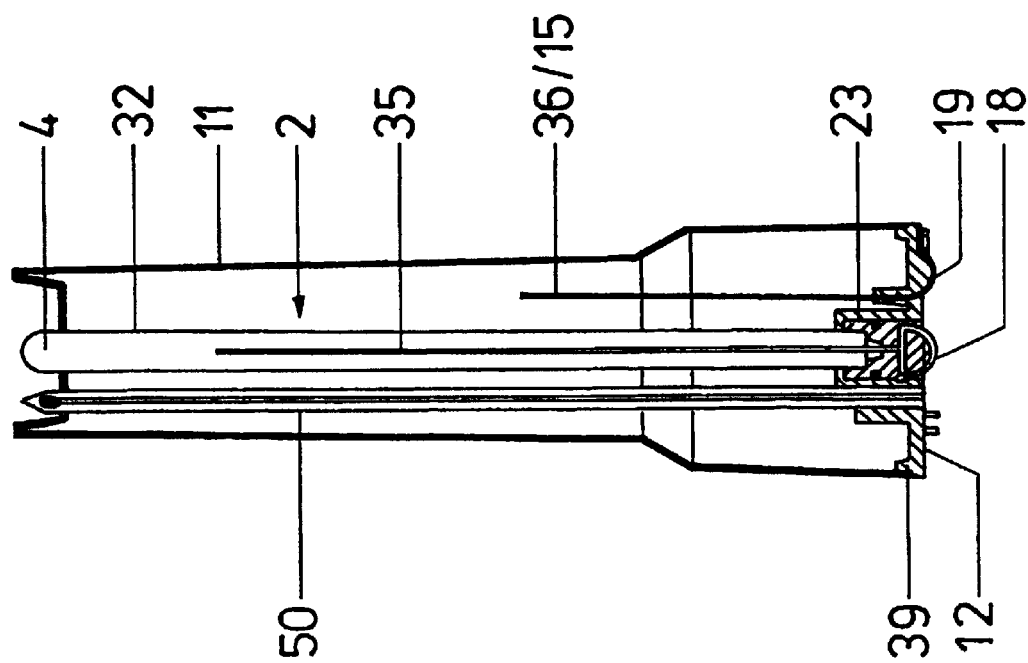

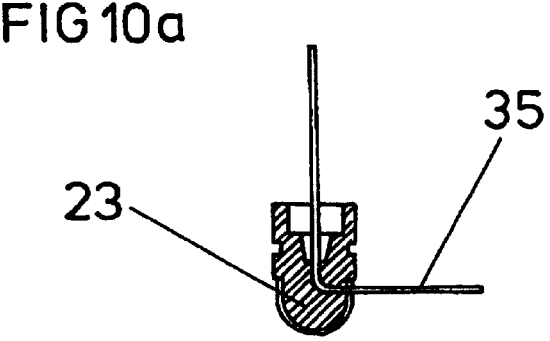
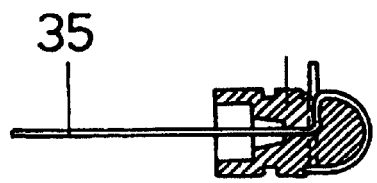
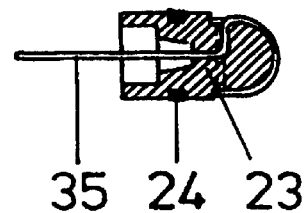
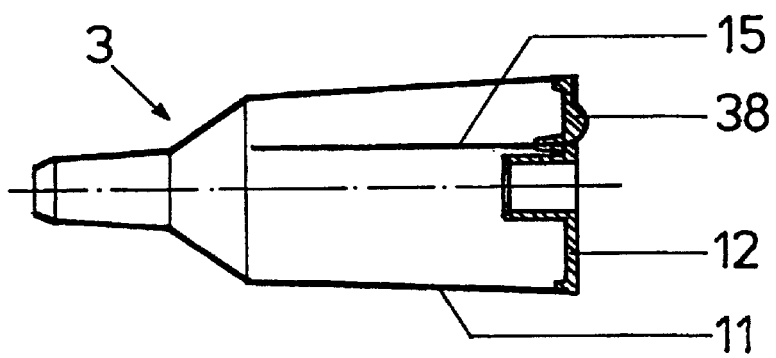
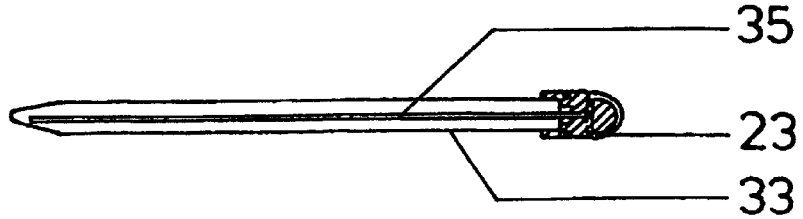
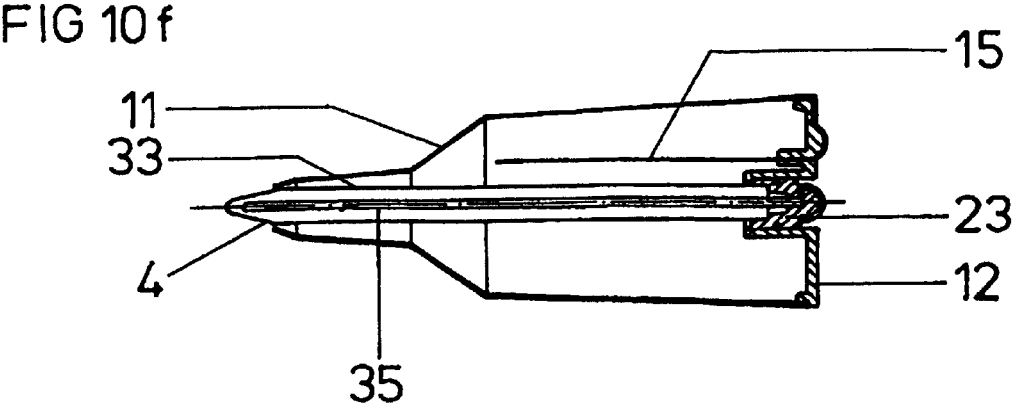

MEASURING DEVICE WITH PENETRATING ELECTRODE

FIELD OF THE INVENTION

The present invention relates to a measuring device having a penetrating electrode. The present invention also relates to a measuring device, a method for manufacturing a measuring device and an application thereof.

BACKGROUND OF THE INVENTION

A measuring device of this type is known from DE 38 14 634 A1, U.S. Pat. Nos. 4,252,124 and 4,218,299.

Such measuring devices are used, for example, to measure the pH of foods such as meat. Usually a chamber is formed between the first electrode and the casing, with a second electrode, usually a gel, accommodated in the chamber. The two electrodes are connected to an analyzer circuit for determining the pH of a liquid of the material to be measured that has penetrated between the electrodes.

First electrodes for pH measurement are usually made of glass or have glass as a casing. For the measurement, the measuring device together with the glass electrode is driven into the material to be measured with great force. The electrode is then subjected to a substantial mechanical stress in the axial direction, i.e., the direction of penetration, e.g., due to the electrode striking a bone. Because of the brittleness of glass, these glass electrodes are able to withstand only a minimal stress, which may often result in breakage, e.g., when they become tilted, during penetration or extraction of the glass electrode or if it is dropped.

To avoid this problem, there are known measuring devices in which the glass electrode and/or the gel surrounding the glass electrode is first enclosed by a glass casing and then by a metal or plastic shell. Although this slightly improves the load-bearing capacity of the glass electrode perpendicular to the axial direction, even the slightest bending of the casing, which is transferred directly to the glass electrode, however, still results in breakage of the glass electrode and/or the glass shell surrounding the electrode.

Because of this double casing of glass and plastic, the measuring device has a disadvantageous thickness in the area of the tip of the probe, so that large holes are produced in the material to be measured by performing the measurement. Furthermore, such measuring devices having thick measuring probes are not suitable for measurements in containers having small insertion openings such as bottles, test tubes and the like.

DE 100 04 583 A1 describes another measuring device of this species having a penetrating electrode. To prevent breakage of the glass electrode, the elongated glass electrode is mounted so that it is pivotable. Therefore the glass electrode may yield to this load to a certain extent in the case of a transverse load perpendicular to its axial direction, so that breakage of the glass electrode is usually prevented in this case. It remains problematical if the glass electrode is additionally or exclusively subjected to a force in the axial direction of the glass electrode, e.g., when it directly strikes a hard bone or drops to the floor. In this case, there is still the risk of breakage of the glass.

Accordingly, it is desirable to provide a measuring device which is designed to be sturdier with respect to loads in the axial direction of the penetrating electrode. Furthermore, a method and an application are also described.

SUMMARY OF THE INVENTION

According to one embodiment of the present invention, the elongated first electrode of the measuring device is mounted so that it is movable in its axial direction and may thus yield to a certain extent into the housing of the measuring device in the event of a load, i.e., an impact in the axial direction. This impact-absorbing characteristic makes it possible in most cases to prevent breakage of the first electrode, which is preferably designed as a glass electrode.

The first electrode is advantageously embedded in a form-fitting manner in a receptacle device.

The receptacle device may be designed, for example, as a recess which has sealing devices on its lateral walls for sealing and securing the first electrode.

According to a first embodiment of the present invention, the receptacle device is made of an elastic material such as rubber which yields in the axial direction when the first electrode presses against the receptacle device.

Additionally or alternatively, the receptacle device may have a damping element which yields in the axial direction when there is pressure on the electrode. The damping element may advantageously be designed as a rubber buffer or as a mechanical spring. However, a pneumatic or hydraulic damping element may also be provided.

In another embodiment of the present invention, the first electrode is inserted into a receptacle device which is part of the base plate of the housing, which is advantageously designed to be elastic. Additionally or alternatively, the base plate may be designed like a diaphragm so that it has folded sections. In the case of a load on the first electrode, the folded sections expand perpendicular to the axial direction so that the base plate thus designed yields and also has a damping effect.

In an advantageous embodiment, the electrodes are electrically connected to contact pins which pass through the base plate. Furthermore, eyes are provided on the outside surface of the base plate. The contact pins here are bent so that they are threadable into these eyes in the base plate. The contact pins which have been bent in this way and threaded into the eyes form contact surfaces associated with the particular electrodes via which the measuring device may be contacted from the outside.

The electrodes may be glued or welded fixedly to the base plate, i.e., the housing. Alternatively, it would also be advantageous, in particular when using a receptacle device, if one end of the electrodes was embedded in a form-fitting manner in a recess in the receptacle device. To this end, the receptacle device typically has sealing and engagement devices for fixation of the first electrode within the receptacle device.

The measuring module has a housing which fixedly surrounds the first electrode and seals it to the outside. The interior of the housing defines a chamber to which an electrode liquid is added, surrounding the first and/or second electrode(s). A polymer protolyte liquid or gel is advantageously provided as the electrode liquid. A measuring module having a polymer protolyte design has the advantage that the measuring range may be expanded to include problematical locations for measurement, e.g., highly polluted wastewater, liquids containing protein, etc. In addition, failures and incorrect potentials are prevented when measurements are performed in such liquids. This prevents blockage or damage in such measurements using traditional pH measuring modules containing a silver-saturated potassium chloride solution as the electrolyte.

In an advantageous embodiment, the measuring probe has a glass tube which contains the first electrode and an electrolyte liquid. When there is a load on the measuring probe, only the glass tube is advanced in the axial direction while the first electrode, which is fixedly attached to the housing, for example, does not move. In another advantageous embodiment, the casing also has a sleeve on the measurement tip of the measuring probe, this sleeve being displaceably arranged with respect to the measuring tip. In this way the measuring tip of the measuring probe may be additionally protected.

In an advantageous embodiment, the measuring device according to the present invention has a slender shaft, which has a much smaller diameter in comparison with the other areas of the housing. In the laboratory area in particular, users of measuring devices are accustomed to slender handling devices such as metering pipettes. Because of this slender design of the measuring device, it is also suitable for measurements in containers having small insertion openings, e.g., bottles, test tubes or other containers. The small tip of the measuring module also permits storage of the measuring probe in a belt holder having an integrated container filled with a storage solution for the electrodes of the pH measuring module.

In a typical embodiment, the first electrode and/or its safety sleeve is made at least partially of glass.

In another very advantageous embodiment, the first electrode is pivotably mounted. The first electrode of the measuring device may thus yield to a certain extent when a load is applied perpendicular to the axial direction of this load, thereby also preventing breakage of the first electrode, which is typically designed as a glass electrode. To this end, the first electrode has pivoting means, e.g., a joint. With regard to the different types of design and functioning of this pivoting electrode, reference is made to DE 100 04 583 A1 cited in the preamble, the full content of which is herewith included in the present patent application.

The casing, i.e., the housing of the measuring module is made at least in part of a material containing SAN or ABS. These are not elastomers but rather plastics which are advantageously elastic in a certain range.

In a very advantageous embodiment, the measuring device has a modular design. This measuring module may thus be attached to a portable pH meter as a part of it. Because of this modular functionality of the measuring module, it may be replaced at any time. If a pH measuring module is nonfunctional, it need merely be replaced while the actual meter may still be used.

The measuring device, i.e., meter, according to the present invention is particularly advantageous in measuring pH in foods, in liquids containing protein or in wastewater. This is possible only by using a polymer protolyte solution in the chamber of the measuring device.

Other advantageous embodiments and refinements of the present invention are evident from the subclaims and the description with reference to the drawing.

BRIEF DESCRIPTION OF THE DRAWINGS

The present invention is explained in greater detail below on the basis of the exemplary embodiments.

FIG. 3 shows a second exemplary embodiment of a measuring module according to the present invention;

FIG. 4 shows a third exemplary embodiment of a measuring module according to the present invention;

FIG. 5 shows a third exemplary embodiment of a measuring module according to the present invention in the unstressed state (FIG. 5a) and in the stressed state (FIG. 5b);

FIG. 8 shows a sixth exemplary embodiment of a measuring module according to the present invention;

FIG. 9 shows a detailed illustration of a base plate;

FIG. 10 shows an advantageous method for manufacturing a measuring module according to FIG. 6;

DETAILED DESCRIPTION OF VARIOUS EMBODIMENTS

The same elements or elements having the same function are labeled with the same reference numbers in all the figures, unless otherwise indicated.

Figure 1:
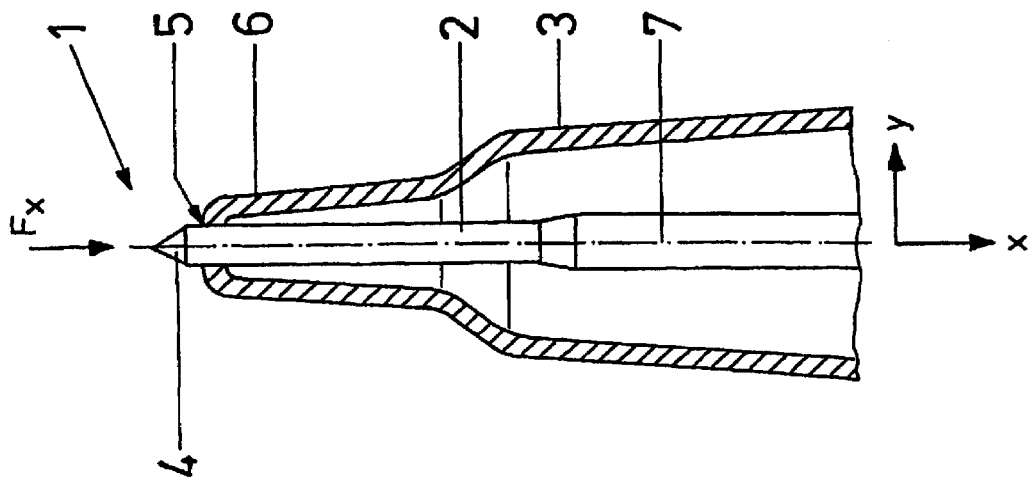
FIG. 1 shows a schematic cross-sectional diagram of a measuring device according to the present invention to illustrate the basic principle of the present invention.

FIG. 1 shows a schematic cross-sectional diagram of a detail of a measuring device according to the present invention, illustrating the principle of the present invention in general terms.

FIG. 1 shows a detail of a measuring device 1 according to the present invention. Measuring device 1 has an elongated first electrode 2 and a housing 3 which encloses first electrode 2 at least partially. A measuring tip 4 of first electrode 2 protrudes here out of an opening 5 provided specifically for this purpose on upper end 6 of housing 3. First electrode 2, typically cylindrical in shape, has a longitudinal axis 7 which defines an axial direction X. According to the present invention, first electrode 2 is movable in axial direction X in relation to housing 3 when acted upon by a force $F_x$.

On the basis of FIGS. 2 through 7, five exemplary embodiments of a measuring device according to the present invention are described below. The measuring device according to the present invention is designed here as a replaceable measuring module 10. Measuring module 10 is designed as a pH measuring module for measuring the pH of liquids, foods, wastewater and the like.

Housing 3 has a casing 11 and a base plate (carrier plate) 12. Casing 11 is preferably made of a relatively elastic plastic. One end 13 of first electrode 2 is joined to base plate 12 while its other end, i.e., measuring tip 4, protrudes out of casing 11 and/or housing 3. First electrode 2 is preferably made of glass or has a glass casing and functions as measuring probe 34 in determining the pH of a material to be measured. The areas between first electrode 2 and housing 3 define a chamber 14. The measuring device also has a second electrode 15, designed here as a silver electrode, protruding from base plate 12 into chamber 14. Chamber 14 is advantageously filled with a polymer protolyte solution.

Housing 3 is sealed tightly toward the outside, except for an inlet for the liquid to be measured. To this end, casing 11 is joined to base plate 12, sealed toward the outside via a sealing device, an adhesive layer, a weld or the like.

Figure 2:
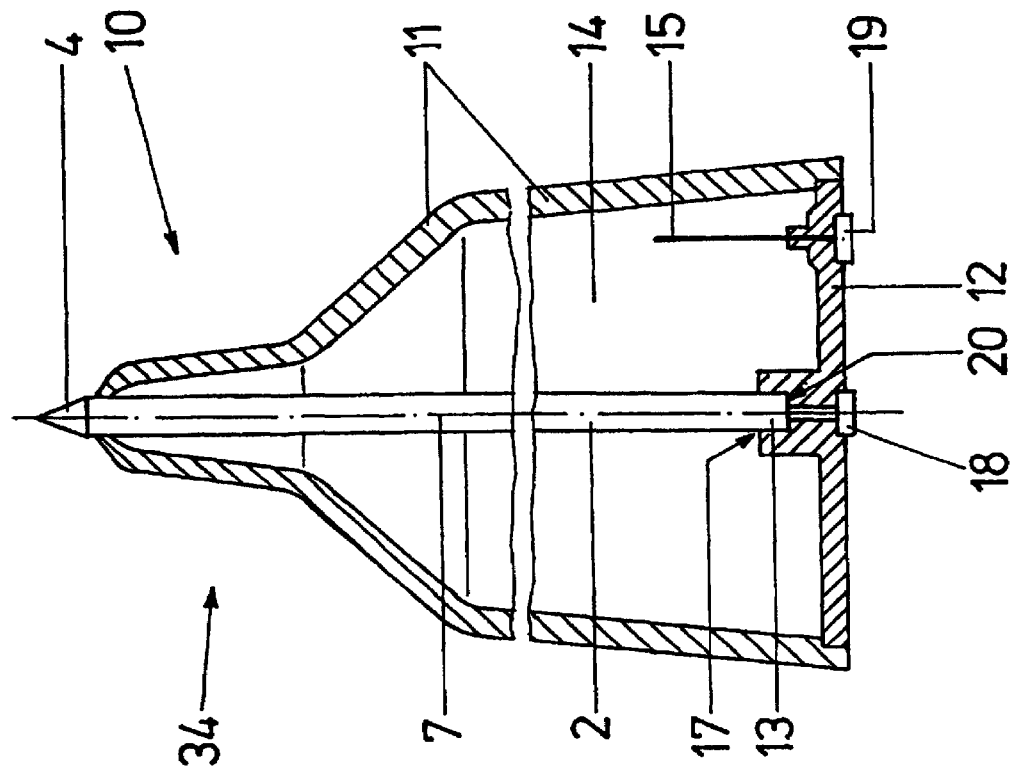
FIG. 2 shows a first exemplary embodiment of a measuring module according to the present invention

In FIG. 2, base plate 12, which is attached to first electrode 2, is made of an elastic material.

Base plate 12 has a recess 17 which accommodates first electrode 2. End 13 of first electrode 2 is inserted in a relatively snug fit into this recess 17, where it is secured by suitable means, e.g., sealing rings, engagement devices, adhesives, etc. Base plate 12 also has contact faces 18, 19, e.g., gold contacts on its outside. First and second electrodes 2, 15 are electrically connected to these contacts 18, 19 by suitable means, to be explained below with reference to FIG. 8.

First electrode 2 rests fixedly on bottom 20 of recess 17 and is thus rigidly connected to base plate 12. If first electrode 2 is acted upon by a force $F_X$ in axial direction X, base plate 12 which is fixedly coupled to first electrode 2 yields in the manner of a diaphragm because of its material properties and in this way dampens the impact caused by force $F_X$. Glass electrode 2 is thereby shifted slightly in axial direction X into housing 3 thereby preventing damage to and/or destruction of glass electrode 2. The exemplary embodiment in FIG. 2 shows the simplest design variant for implementation of a measuring module 10 according to the present invention which is advantageous in particular from the standpoint of assembly and for cost reasons.

In contrast with the variant in FIG. 2, measuring module 10 in FIG. 3 has a base plate 12 designed like a diaphragm. Base plate 12 has folded sections 21; in the case of an impact $F_X$ in axial direction X, these folded sections dampen this impact by expanding perpendicular to axial direction X, i.e., in direction Y.

In contrast, a spring 22 is provided in the exemplary embodiment in FIG. 4. This spring 22 is situated between glass electrode 2 and base plate 12. Spring 22 is secured in base plate 12 by a receptacle device 23 provided specifically for this purpose and is sealed to the outside by an O-ring 24.

In the exemplary embodiment of FIGS. 5a, 5b, a rubber buffer 25 is provided. Rubber buffer 25 is made of an elastic compressible material, e.g., rubber or a spongy material. Rubber buffer 25 protrudes into chamber 14 through an opening provided specifically for this purpose in base plate 12. At its upper end 48 which protrudes into chamber interior 14, rubber buffer 25 has a recess 26 into which end 13 of glass electrode 2 is inserted in a form-fitting manner. This end 13 rests on bottom 27 of this recess 26 and is positioned in recess 26 by peripheral sealing lips 28 provided on lateral faces 29 of recess 26. On the other side 49 of rubber buffer 25 where it protrudes through an opening in base plate 12, a peripheral O-ring 24 is provided for sealing it from the outside.

The functioning of measuring module 10 is explained below on the basis of FIGS. 5a, 5b:

For the measurement, measuring probe 34 of measuring module 10 is introduced into material 16 to be measured, as illustrated in FIG. 5b, for example. Through suitable measures, not explained further here, e.g., through a diaphragm, liquid of material 16 to be measured enters the area between first electrode 2 and second electrode 15. To facilitate the introduction into material 16 to be measured, measuring probe 34 has a penetrating tip 4 on its end which protrudes out of measuring module 10. A force $F_x$ in axial direction X is exerted on glass electrode 2 by insertion into material 16 to be measured. The damping of the damping element designed as a rubber buffer 25 is such that by simply inserting it into material 16, e.g., meat that is to be measured, glass electrode 2 is pushed into housing 3 in axial direction X only to an insignificant extent or none at all. However, if glass electrode 2 strikes a hard object, e.g., a bone, in material 16 to be measured, then axial force $F_X$ exerted by this bone on glass electrode 2 will be great enough to push glass electrode 2 slightly into housing 3 in axial direction X. The elasticity of rubber buffer 25 is such that force $F_X$ is sufficient to deform, i.e., compress, rubber buffer 25. Because of this deformation, i.e., compression, of rubber buffer 25, glass electrode 2 is pushed into housing 3 and in this way is protected from damage or destruction. The same effect occurs when the measuring tip 4 of measuring module 10 is subjected to a sudden impact such as that which occurs, for example, when it drops to the floor.

In the exemplary embodiments according to FIGS. 2 and 3, a base plate 12 is provided as a damping element; in the exemplary embodiment in FIG. 4 a spring 22 is provided as a damping element, and in the exemplary embodiment in FIG. 5 a rubber buffer 25 is provided as a damping element. In the exemplary embodiments according to FIGS. 4 through 5, the base plate 12 is made of a solid material which has dimensional stability and will not undergo deformation under a force impact $F_X$. However, it would also be conceivable to use a flexible elastic material for base plate 12 as in Example 2, because this would further improve the damping effect.

Figure 6:
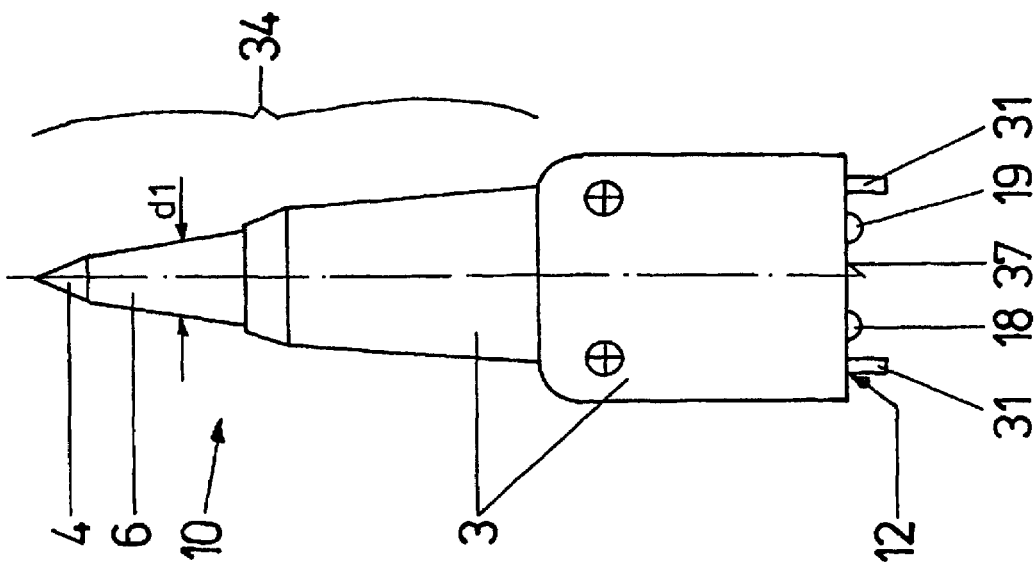
FIG. 6 shows the housing of a measuring module according to the present invention.

FIG. 6 shows a complete housing 3 of a measuring module 10 designed according to a modular design. This measuring module 10 may be designed, for example, as shown in FIGS. 2 through 5. Contact faces 18, 19 are provided on bottom side 37 of base plate 12. On this side 37, base plate 12 also has plug connectors 31 via which measuring module 10 may be attached to a meter (not shown in FIG. 6). Measuring module 10 has a measuring probe 34. This measuring probe 34 tapers in the direction of measuring tip 4, so that measuring probe 34 has a much smaller diameter d1 at upper end 6 of housing 3 than in the lower area facing base plate 12. Measuring probe 34 may therefore also be inserted into bottles, test tubes or other containers having an opening of a smaller diameter.

Figure 7:
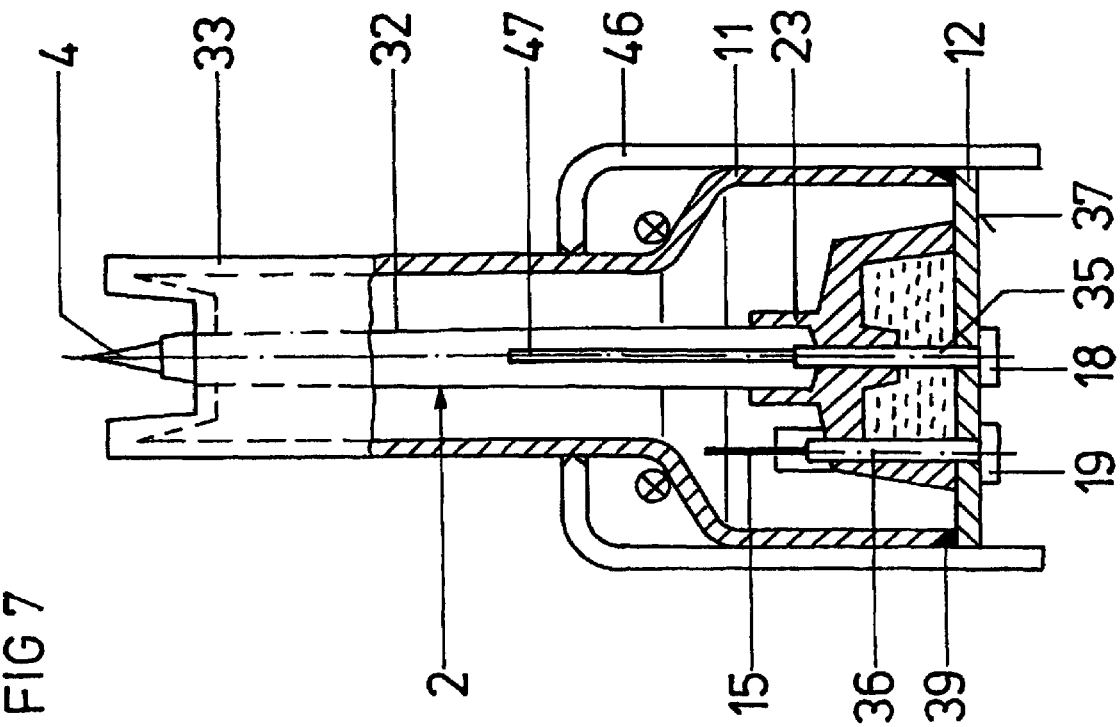
FIG. 7 shows a fifth exemplary embodiment of a measuring module according to the present invention.

The exemplary embodiments according to FIGS. 2 through 5 illustrate a first electrode 2 designed as a glass electrode. It would also be conceivable according to FIG. 7 if measuring probe 34 were made of a silver rod 47 with a glass tube 32 surrounding this silver rod 47. An electrolyte liquid is typically added between silver rod 47 and glass tube 32. Additionally or alternatively, housing 3 may have a protective shell on its upper end 6, protecting housing 3 of measuring module 10 toward the outside, e.g., from mechanical stress, moisture or the like. In contrast with the exemplary embodiments illustrated in FIGS. 2 through 5, glass tube 32 inserted into measuring module 10 from above is glued in its anchoring in receptacle device 32. Additionally or alternatively, housing 3 may have safety webs 33 which provide additional protection for measuring probe 32 on its upper end 6 (FIGS. 7, 8).

Because of these protective webs, measuring probe 34 no longer has the pointed measuring tip 4, which is advantageous for insertion into material 16 to be measured according to the exemplary embodiment in FIG. 8, but it is optimally protected. Meter 10 here is suitable in particular for measurements in liquids and is therefore advantageously used as a laboratory meter. Measuring tip 4 is typically rounded for this reason. In addition, FIG. 8 shows a tube 50 which tapers to a pointed end at the measuring tip and is fixedly connected to the base plate 12 at one end and at the other end protrudes out of housing 3. This pointed tube 50, advantageously made of stainless steel, contains a temperature sensor and is used for determining the temperature of material 16 to be measured.

FIG. 9 shows a detailed diagram of base plates 12 and electrodes 2, 15 anchored therein. Electrodes 2, 15 are rigidly connected to base plate 12, either by gluing the electrodes in receptacle device 23 according to FIGS. 7 through 9 or by inserting in a form-fitting manner into receptacle devices 23 according to FIGS. 2 through 5. An electrically conducting rod 35, 36 connected to electrodes 2, 15 protrudes through base plate 12. On bottom side 32 of base plate 12, it has injection-molded eyes 38. To maintain defined contact faces 18, 19, one rod 36 is looped into an eye 38, whereas the other rod 35 is suitably bent around receptacle device 23 which is provided in base plate 12.

Electrode 15, which is encased in base plate 12, forms second electrode 15 together with the polymer protolyte gel that is introduced into chamber 14 and is situated between housing 3 and measuring probe 2.

An advantageous method for manufacturing a measuring module 10 is described below with reference to FIG. 10:

(a) Rod 35 of electrode 1 is first encased in a plastic material, for example, which then forms receptacle device 23.

(b) Rod 35 protruding outward is then bent suitably. To do so, the end of rod 35 protruding outward is bent or looped around encased plastic body 23 so that rod 35 is fixedly secured while forming a contact that is electrically contactable from the outside. Protruding ends of contact rod 35 are cut off if necessary. The end of rod 35 pointing outward may also be aligned suitably at this opportunity.

(c) An O-ring 24 is attached to receptacle device 23.

(d) Casing 11 of measuring module 10 is encased separately. Encasing second rod 36 in a plastic material, for example, which forms base plate 12. The contact rod which should form second electrode 15 is bent on its outer end and looped into an eye 38 provided specifically for this purpose in base plate 12. Base plate 12 and casing 11 are joined together fixedly by ultrasound welding to form housing 3.

(e) A glass tube 33 is provided, an electrode liquid being added to it. Glass tube 33 is then glued in receptacle device 23. Glass tube 33 with electrode liquid contained in it as well as contact rod 35 form first electrode 2.

(f) Finally, this first electrode 2 together with receptacle device 23 is inserted into chamber 14 of housing 3 while it is still empty and is secured there in a suitable way. A sealing device (O-ring 24) seals housing 2 on the side of base plate 12 from the outside.

Figure 11:
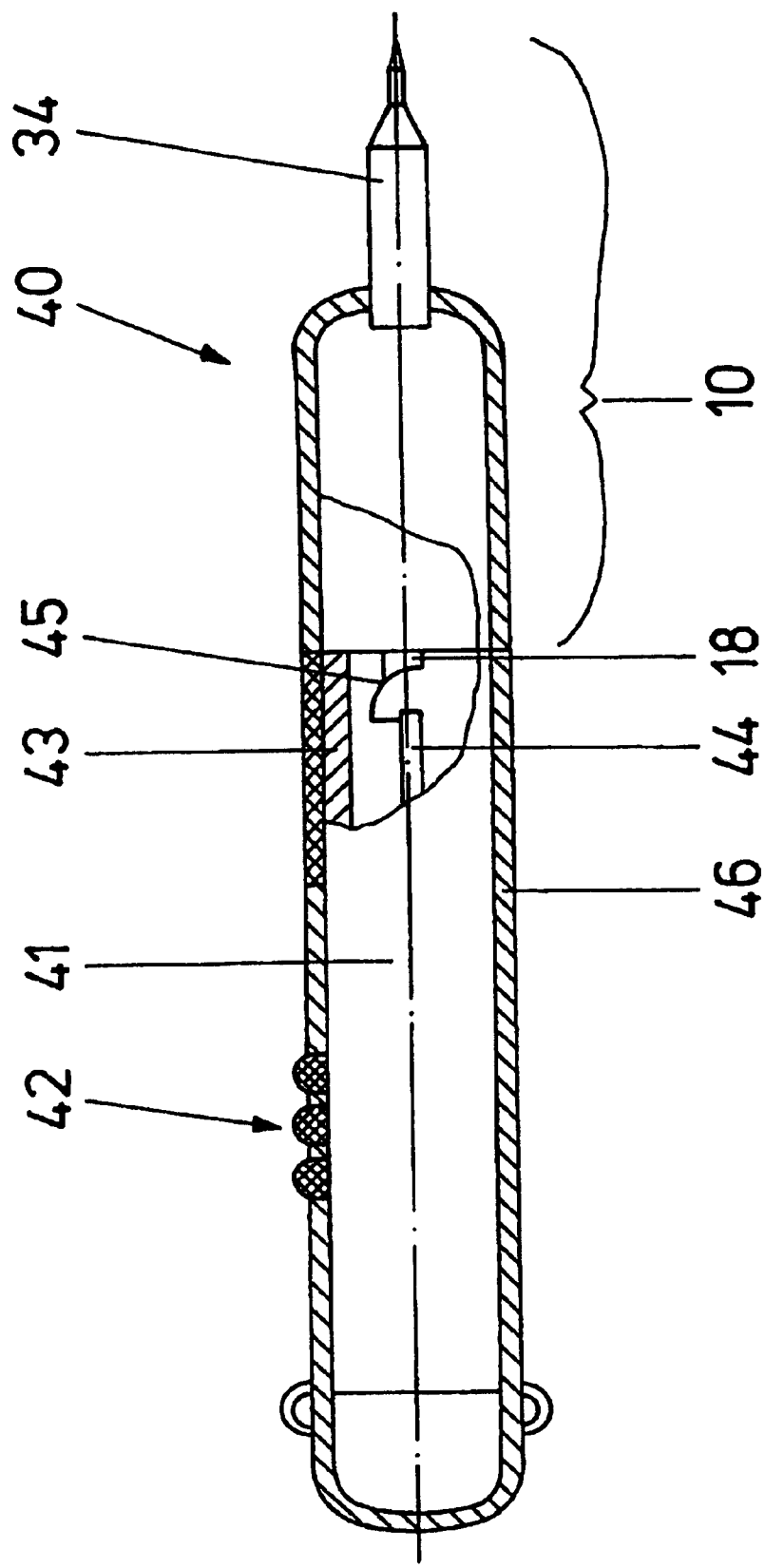
FIG. 11 shows a cross-sectional diagram of a meter having a measuring module according to the present invention attached to it modular style.

FIG. 11 shows a cross-sectional diagram of a portable meter 40. Meter 40 has a housing 41 on which a pH measuring module 10 is mounted. For example, pH measuring module 10 is designed according to the measuring modules illustrated in FIGS. 2 through 7 and has contact faces 18 on the bottom side of base plate 12.

Meter 40 has a keyboard 42 for input of data and a display 43 for displaying measurement results and data. A circuit board 44 is provided inside housing 41. Circuit board 44 is contactable to corresponding contact faces 18 of measuring module 10 via connecting lines, which are designed here as spring contacts 45. In this way, pH measuring module 10 is electrically adapted to meter 40.

Meter 40 having measuring module 10 is advantageously provided with an elastic protective shell 46 for reasons of stability, compactness and hygiene, the shell being designed to be transparent or at least partially transparent at least in the area of display 43.

In summary, by using a measuring electrode that is movable in its axial direction, it is possible to protect it very easily but nevertheless very effectively against destruction and/or damage when there is an impact directed in the axial direction.

The present invention has been explained on the basis of the exemplary embodiments described above so that the principle of the present invention and its practical application may be explained in the best possible way, but the present invention may of course also be implemented in a modified version in a variety of other embodiments.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A measuring device, comprising:
    an elongated first electrode having a longitudinal axis for insertion into a material to be measured;
    a housing which at least partially surrounds the first electrode, wherein the first electrode is movable in relation to the housing in the axial direction of the longitudinal axis;
    a receptacle device that accommodates an end of the first electrode, wherein the housing has a base plate on a side of the receptacle device and the receptacle device is part of the base plate, and wherein the base plate is made of an elastic material;
    a chamber which is enclosed by the housing and is tightly sealed with respect to the outside, wherein the base plate tightly seals a lower area of the chamber; and
    contact rods, wherein at least one of the contact rods is connected to the first electrode, and wherein the contract rods protrude through a base plate and are bent on a bottom side of the base plate so that the bent ends of the contact rods are threaded into eyes provided on the bottom side of the base plate.

2. The measuring device as recited in claim 1, wherein the receptacle device is made of an elastic material which yields in the axial direction with a movement of the first electrode.

3. The measuring device as recited in claim 1, wherein the receptacle device has a damping element or is connected to a damping element which yields in the axial direction with a movement of the first electrode and thereby exerts a force directed in the opposite direction on the end of the first electrode.

4. The measuring device as recited in claim 3, wherein the damping element is designed as a rubber buffer.

5. The measuring device as recited in claim 3, wherein the damping element is designed as a spring.

6. The measuring device as recited in claim 1, wherein the base plate is designed like a diaphragm and has folded sections.

7. The measuring device as recited in claim 1, wherein the receptacle device has a recess for form-fittingly receiving one end of the first electrode.

8. The measuring device as recited in claim 7, further comprising a sealing device through which the one end of the first electrode is in tight contact with the recess.

9. The measuring device as recited in claim 1, wherein the first electrode is glued or welded to the housing or is encased.

10. The measuring device as recited in claim 1, further comprising at least one second electrode provided between the first electrode and a casing.

11. The measuring device as recited in claim 10, wherein a polymer protolyte liquid is added to the chamber, surrounding at least one of: the first and second electrodes.

12. The measuring device as recited in claim 1, wherein the first electrode is situated in a tube to which an electrolyte liquid is added.

13. The measuring device as recited in claim 12, wherein the tube is displaceable in the axial direction toward the first electrode.

14. The measuring device as recited in claim 1, wherein the housing is displaceably situated on a measuring tip with respect to the first electrode.

15. The measuring device as recited in claim 1, wherein a diameter of the housing decreases in the direction of a measuring tip of the first electrode.

16. The measuring device as recited in claim 1, wherein at least one of:
the first electrode and a protective sleeve surrounding the first electrode is made at least partially of glass.

17. The measuring device as recited in claim 1, wherein the first electrode is pivotably mounted.

18. The measuring device as recited in claim 17, wherein the first electrode has pivoting means via which the first electrode is pivotable away from the axial direction in the case of a force component perpendicular to the axial direction.

19. The measuring device as recited in claim 1, wherein the housing contains at least in part a SAN or ABS material.

20. The measuring device as recited claim 1, further comprising:
at least one second electrode disposed between the first electrode and the housing.

21. A portable pH meter having a modular replaceable pH measuring device, wherein said measuring device includes:
an elongated first electrode having a longitudinal axis for insertion into a material to be measured;
a housing which at least partially surrounds the first electrode, wherein the first electrode is movable in relation to the housing in the axial direction of the longitudinal axis;
a receptacle device that accommodates an end of the first electrode, wherein the housing has a base plate on a side of the receptacle device and the receptacle device is part of the base plate, and wherein the base plate is made of an elastic material;
a chamber which is enclosed by the housing and is tightly sealed with respect to the outside, wherein the base plate tightly seals a lower area of the chamber; and
contact rods, wherein at least one of the contact rods is connected to the first electrode, and wherein the contract rods protrude through a base plate and are bent on a bottom side of the base plate so that the bent ends of the contact rods are threaded into eyes provided on the bottom side of the base plate.

22. The pH meter as recited in claim 21, further comprising a display and a keyboard situated in said housing and a circuit board from which spring contacts lead away to contacts of the first electrode and a second electrode, the contacts being situated on a bottom side of a base plate.

23. The portable pH meter as recited in claim 21, wherein the contact rods are electrically conducting and are encased to form the base plate, and wherein the contact rods protrude from the base plate to form the first electrode.

24. The portable pH meter as recited in claim 21, further comprising:
a tube including an electrode liquid, wherein the first electrode is inserted into the tube and the tube is attached to the base plate.

25. The portable pH meter as recited in claim 21, wherein the base plate is welded to the housing.

26. The portable pH meter as recited in claim 21, wherein the chamber includes a polymer protolyte liquid.

27. The portable pH meter as recited in claim 21, wherein the contact rods protruding out of the housing are bent over to form contacts on the outside wall of the housing.

28. A method for measuring pH, comprising:
inserting a measuring device into a material to be measured, wherein said measuring device includes:
an elongated first electrode having a longitudinal axis for insertion into a material to be measured;
a housing which at least partially surrounds the first electrode, wherein the first electrode is movable in the axial direction of its longitudinal axis, and wherein said first electrode is surrounded by a polymer protolyte material;
a receptacle device that accommodates one end of the first electrode, wherein the housing has a base plate on a side of the receptacle device and the receptacle device is part of the base plate, and wherein the base plate is made of an elastic material;
a chamber which is enclosed by the housing and is tightly sealed with respect to the outside, wherein the base plate tightly seals a lower area of the chamber; and
contact rods, wherein at least one of the contact rods is connected to the first electrode, and wherein the contract rods protrude through a base plate and are bent on a bottom side of the base plate so that the bent ends of the contact rods are threaded into eyes provided on the bottom side of the base plate.

29. The method of claim 28, wherein the first electrode is movable with respect to the housing in the axial direction of the longitudinal axis.

* * * * *

UNITED STATES PATENT AND TRADEMARK OFFICE
CERTIFICATE OF CORRECTION

| | | |
|---|---|---|
| PATENT NO. | : 7,604,723 B2 | Page 1 of 1 |
| APPLICATION NO. | : 10/511418 | |
| DATED | : October 20, 2009 | |
| INVENTOR(S) | : Andreas Derr | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1273 days.

Signed and Sealed this

Fifth Day of October, 2010

David J. Kappos
*Director of the United States Patent and Trademark Office*